United States Patent
Stanton, Jr. et al.

(10) Patent No.: US 6,401,043 B1
(45) Date of Patent: Jun. 4, 2002

(54) VARIANCE SCANNING METHOD FOR IDENTIFYING GENE SEQUENCE VARIANCES

(75) Inventors: Vincent P. Stanton, Jr., Belmont; Robert Mark Adams, Natick, both of MA (US); David Steffen, Houston, TX (US)

(73) Assignee: Variagenics, Inc., Cambridge, MA (US)

(*) Notice: Subject to any disclaimer, the term of this patent is extended or adjusted under 35 U.S.C. 154(b) by 0 days.

(21) Appl. No.: 09/419,705

(22) Filed: Oct. 14, 1999

Related U.S. Application Data

(63) Continuation-in-part of application No. 09/300,747, filed on Apr. 26, 1999, now abandoned.
(60) Provisional application No. 60/131,334, filed on Apr. 26, 1999.

(51) Int. Cl.[7] ............ G01N 33/48; C12Q 1/68; C12P 19/34
(52) U.S. Cl. ............ 702/20; 435/6; 435/91.1; 435/91.2
(58) Field of Search ............ 435/6, 91.1, 91.2; 702/20

(56) References Cited

U.S. PATENT DOCUMENTS 5,873,052 A * 2/1999 Sharaf ............ 702/20
5,972,602 A * 10/1999 Hyland et al. ............ 435/6

OTHER PUBLICATIONS

Taillon–Miller et al., "Overlapping Genomic Sequences: A Treasure Trove of Single–Nucleotide Polymorphisms," Genome Research, Jul. 1998, vol. 8, Issue 7, pp. 748–754.*
Reider et al., "Automating the identification of DNA variations using quality–based fluorescence re–sequencing: analysis of the human mitochondrial genome," Nucleic Acids Research, 1998, vol. 26, No. 4, pp. 967–973.*

* cited by examiner

*Primary Examiner*—John S. Brusca
*Assistant Examiner*—Young Kim
(74) *Attorney, Agent, or Firm*—Fish & Richardson P.C.

(57) ABSTRACT

The present disclosure describes methods for the computational analysis of genetic variances in the coding and non-coding regions of particular genes.

19 Claims, 6 Drawing Sheets

FIG. 7

```
                1661                                                                                                    .
GEN-42M:     GATTTTCTGCCA_GGCGTG_TGTTACAGCAG_TTTGCAGAT_AAT_GATG_TG_TCAA_GATTCAA_GGCAATTAA___GGCT_CGTTTT_GCAAAACCA

W27785 010:  GnTTnTCTGCCA_GGCGTG_TGTTACAGCAG_TTTGCAGAT_AAT_GATG_TC_TCAA_GATnCAA_GGnAGTTAn__GGnT_CGATTT_GGAAAACCA
H49807 022:  GATTTTCTGCCG_GGCGTG_TGTTACAGCAG_TTTGCAGAT_AAT_GATG_TG_TCAA_GATTCAA_GGCAGTTAA___GGCT_CGTTTT_GCAAAACCA
N77535 022:  GATTTTCTGCCA_GGCGTG_TGTTACAGCAG_TTTGCAGAT_AAT_GATG_TG_TCAA_GATTCAA_GGCAGTTAA___GGCTCCGTTTT_GCAAAACCA
N80977 022:  GATTTTCTGCCA_GGCGTG_TGTTACAGCAG_TTTGCAGAT_AAT_GATG_TG_TCAA_GATTCAA_GGCAGTTAA___GGCT_CGTTTT_GCAAAACCA
R93690 022:  GATTTTCTGCCA_GGCGTG_TGTTACAGCAG_TTTGCAGAT_AAT_GATG_TG_TCAA_GATTCAA_GGCGATTAA___GGCT_CGTTTT_GCAAAACCA
H14398 023:  GATTTTCTGCCAGGGGCGTGTGTTGTTACAGCAGTTTTGCAGATAAATGGATGTTGTTCAAGGTTTCAAGGGGCGATTAAAAGGCT_CGTTTTGGCAAAACCA
N49118 029:  GATTTTCTGCCA_GGCGTG_TGCTACAGCAG_TTTGCAGAT_AAT_GATG_TG_TCAA_GATTCAA_GGCGGTTAA___GGCT_CGTTTT_GCAAAACCA
AA460574 035:GATTTTCTGCCA_GGCGTG_TGTTACAGCAG_TTTGCAGAT_AAT_GATG_TG_TCCA_GATTCAG_GGCN
T53189 037:  GATTTTCTGCCA_GGCGTG_TGTTACAGCAG_TTTGCAGAT_AAT_GATG_TG_TCAA_GATTCAA_GGCAGTTAA___GGCT_CGTTTT_GCAAAACCA
 -------------------------------------------------------------------------------------------------
Tot.Obs.Var.:  A  T     GG           T  C          T      A  G     T CT       G TT  G  CGG    AA  C C  A   G G
After Filter:                                                                                     G
```

VARIANCE SCANNING METHOD FOR IDENTIFYING GENE SEQUENCE VARIANCES

RELATED APPLICATIONS

This application claims the benefit of Stanton et al., U.S. Provisional Appl. No. 60/131,334, filed Apr. 26, 1999, entitled GENE SEQUENCE VARIANCES WITH UTILITY IN DETERMINING THE TREATMENT OF DISEASE, and is a continuation-in-part of U.S. patent application, Stanton and Adams, Ser. No. 09/300,747, now abandoned filed Apr. 26, 1999, entitled GENE SEQUENCE VARIANCES WITH UTILITY IN DETERMINING THE TREATMENT OF DISEASE, which are hereby incorporated by reference in their entireties, including drawings.

BACKGROUND OF THE INVENTION

This application concerns the field of identification of genetic variances in genomes of mammalians. In the cases of gene sequence variances within the human genome in human populations, the identification of said sequence variation has utility in determining response to drug therapy.

Many drugs or other treatments are known to have highly variable safety and efficacy in different individuals. A consequence of such variability is that a given drug or other treatment may be highly effective in one individual, and ineffective or not well tolerated in another individual. Thus, administration of such a drug to an individual in whom the drug would be ineffective would result in wasted cost and time during which the patient's condition may significantly worsen. Also, administration of a drug to an individual in whom the drug would not be tolerated could result in a direct worsening of the patient's condition and could even result in the patient's death.

For some drugs, up to 99% of the measurable variation in selected pharmacokinetic parameters has been shown to be inherited, or associated with genetic factors. For a limited number of drugs, discrete gene sequence variances have been identified in specific genes that are involved in drug action, and these variances have been shown to account for the variable efficacy or safety of the drug in different individuals.

The exponentially growing number of publicly available expressed sequence tags (ESTs) have led to the development of approaches to rapidly identify high-throughput methods for the detection of single nucleotide polymorphisms (SNPs). These methods focus on the manipulation of available sequence data to identify the most common form of DNA sequence variation, SNPs. Sequence fragments from many different individuals can be assembled into overlapping sequence assemblies and genetic differences at the single nucleotide base level can be identified. A variety of different techniques have been developed for rapidly identifying potential SNPs from these assemblies and for scoring these polymorphisms in such a way to distinguish them from sequencing error or other experimental artifact. In such a way, sequence scanning can identify potentially informative genetic markers which can then be correlated to physiologic function, pathophysiologic disease, or drug or therapeutic intervention response.

Manual methods to determine the polymorphisms within a gene or gene family are best suited for a gene or gene family having small numbers of base pairs. This method is user or investigator dependent and requires significant effort in the analysis and interpretation.

Automated methods that make use of sequencing chromatograms to assist in the determination of quality and locations of polymorphisms allow analysis of additional sequences. Unfortunately, automated polymorphism detection is complemented with visual inspection of the chromatogram traces and such methods are best suited for polymorphism detection in gene families or in genomic loci where the base pair number is in the tens of thousands. A further limitation to this method is that not all chromatograms are available for each of the ESTs. Thus, this method may frequently require further substantial sequence data and corresponding information.

In establishing a link between drug response and genetic polymorphism, one must use all available ESTs and thus a computational method for the high-throughput analysis of this sequence data for the identification of these potentially critical genetic polymorphisms. Not all of the identified differences in the ESTs data are SNPs, therefore, it is critical to establish reasonable and statistically stringent strategies to ensure that this analysis results in SNP detection within legitimate confidence limits.

Recently there have been several papers describing computational methods for the detection of genetic polymorphism. One, (Picoult-Newberg et al.) describes a staged-filter model. The method employs the sequence alignment capabilities of the PHRAP computer program (Phil Green, University of Washington) for assembly, and does not attempt to optimize this step. The method also utilize certain calculations in order to remove patches of low-quality sequence having particular characteristics. The method does not include use of any statistical scoring techniques, relying instead on confirmation by laboratory methods.

A second (Buetow et al.) method utilizes sequence data for which quality scores and chromatograms are available that is used as the basis for assembly, again with the use of the PHRAP program. Certain calculations are performed to remove particular types of low-quality sequence. The method makes use of the quality and chromatogram data within these processes, presumably to improve error rates, at the cost of not being able to use sequence data directly from the database, especially sequence data for which such additional information may not be available. The method follows the filtration process with a statistical scoring method based on Baysian statistics.

SUMMARY OF THE INVENTION

The inventors have determined that the identification of gene sequence variances within genes that may be involved in drug action is important for determining whether genetic variances account for variable drug efficacy and safety and for determining whether a given drug or other therapy may be safe and effective in an individual patient. Provided in this invention is a method for the identification of such gene sequence variances which can be useful in connection with predicting differences in response to treatment and selection of appropriate treatment of a disease or condition.

In the present invention, we have identified a computational method for the rapid determination of genetic sequence variation for the purposes of determining the correlation of drug response with genetic variation for a population. In addition, the method can also be used in other applications for which detection of sequence variances is desired. This invention has utility, for example, in programs including drug development, medical management programs, and retrospective analysis of a human population to drug therapy.

In a first aspect, this invention provides a method for identifying at least one variance in at least one gene. The method involves obtaining at least three independent electronic nucleic acid sequences with sequence overlap regions for each gene, comparing the sequence overlap regions for each gene to identify sequence differences; and analyzing the sequences or sequence differences or both to discriminate sequencing errors from sequence variances for each said gene.

Preferably the analyzing includes comparing the at least 3 electronic nucleic acid sequences to identify sequence differences between said sequences, and then applying at least one of the following filters that are helpful for distinguishing true variances from artifacts or sequence errors. One filter involves identifying and removing or discounting sequence differences in portions of the sequences in which the number of sequence differences in an analysis window exceeds a predetermined limit. A second filter involves identifying and removing or discounting of consecutive mismatches. A third filter involves assigning sequence differences a probability of representing a true variance based on sequence context. A fourth filter involves performing a calculation utilizing the detection of particular sequence differences at the same sites in multiple sequences as an indication that each such sequence difference represents a true variance. Preferably the analysis result is a score that is derived from the probability that a detected sequence difference represents a true variance, the above filters can be used singly or in any combination, and can also be used with other filters or sequence quality information.

Thus, in preferred embodiments, the variance scanning method of this invention generally follows four steps. First, the cDNA fragment sequences (ESTs) which are all derived from the same gene are clustered together. Similarly, any set of sequences from a gene can be assembled, e.g., genomic sequences or cDNA sequences. Second, those sequences are aligned together, either by multiple alignment methods (e.g. PHRAP) or by iterative pairwise alignment. Third, areas of poor sequence quality are filtered out by a variety of processes, removing cases where observed sequence polymorphism is artifact due to error. Fourth, the remaining sites of polymorphism are scored on the basis of the likelihood that they represent true polymorphism rather than artifact. This fourth step generally employs information from multiple sequences in the alignment at the point of variation, and has the capacity to employ statistical models for purposes of validation. The sensitivity and selectivity of variance detection by this method are typically greater for genes in which the sequence data, e.g., EST data, is complete along the whole sequence, rather than concentrated in the 3' end, as is the case with most publicly available EST data.

In the context of this invention, "true polymorphisms" or "true variances" are polymorphisms or variances which actually occur in the nucleic acid of individuals as compared to other individuals. This is distinguished from apparent or detected polymorphisms or variances which appear as differences in representations (generally electronic representations) of nucleic acid sequences, and which may represent true variances or may represent artifacts due to sequencing errors or other errors and do not represent actual nucleic acid sequence differences in the individuals from whom the sequence was determined.

Variances occur in the human genome at approximately one in every 500–1,000 bases within the human genome when two alleles are compared. When multiple alleles from unrelated individuals are compared the frequency of observation of variant sites increases. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites.

Determining the presence of a particular variance or plurality of variances in a particular gene in a population can be performed in a variety of ways. The term "computational method" refers to a set of algorithms performed in a prescribed order.

The term "filter" as used herein is an algorithm intended to exclude base pair mismatches observed between sequences to enhance the likelihood that base pair mismatches which pass the filter represent true variances rather than artifacts, e.g., sequencing artifacts.

The term "discount sequence differences" or phrases of like import which refer to discounting observed variances or sequence differences between two or more sequences is intended to reflect the treatment of identified sequence differences that are not considered further, or are assigned a lower probability or weighting than would otherwise be utilized, in computational filters, algorithms, or in the results obtained.

The process of "identifying" or discovering new variances involves analyzing the sequence of a specific gene in at least two alleles, more preferably at least 3, 5, 7, 8, or 10 alleles, still more preferably at least 12, 15, 20, 30, or 40 alleles, and most preferably at least 50 alleles, or from at least that number of individual cell sources. The analysis of large numbers of individuals to discover variances in the gene sequence between individuals in a population will result in detection of a greater fraction of all the variances in the population. Typically, independent sequences reported in sequence databases represent sequencing from independent alleles. Thus, in the various aspects of this invention, in preferred embodiments, the numbers of independent sequences corresponding to a gene are utilized as just indicated for sequence variance in multiple alleles are utilized.

In the various aspects of this invention, preferably sequence information from at least 100 genes is analyzed, more preferably at least 500, 1000, 2000, 3000, 5000, 7000, 10000, or even more.

The sequence information is preferably for cDNA or genomic DNA. The organism can be any organism for which multiple sequences are available, but is preferably from a mammal, more preferably from human.

Preferably the process of identifying reveals whether there is a variance within the gene; more preferably identifying reveals the location of the variance within the gene; more preferably identifying provides knowledge of the sequence of the nucleic acid sequence of the variance, and most preferably identifying provides knowledge of the combination of different variances that comprise specific variant forms of the gene or alleles. In identifying new variances it is often useful to screen different population groups based on race, ethnicity, gender, and/or geographic origin because particular variances may differ in frequency between such groups. It may also be useful to screen DNA from individuals with a particular disease or condition of interest because they may have a higher frequency of certain variances than the general population.

The term "genotype" in the context of this invention refers to the particular allelic form of a gene, which can be defined by the particular nucleotide(s) present in a nucleic acid sequence at a particular site(s).

The terms "variant form of a gene", "form of a gene", or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants". The term "alternative form" refers to an allele that can be distinguished from other alleles by having distinct variances at least one, and frequently more than one, variant sites within the gene sequence.

Other terms known in the art to be equivalent to "variances" include mutation and single nucleotide polymorphism (SNP). In this invention, the variances are selected from the group as identified through the use of a computational method. Reference to the presence of a variance or variances means particular variances, i.e., particular nucleotides at particular polymorphic sites, rather than just the presence of any variance in the gene.

The terms "variance scanning", or "scanning" refers to the method of rapidly determining whether there are nucleotide sequence differences between one or more of cDNA or genomic samples from one or more individuals or population samples. Preferably the method utilizes a computationally-based approach, e.g., as described herein.

In preferred embodiments in which a plurality of variances is determined, the plurality of variances can constitute a haplotype or haplotypes.

In the context of this invention, the term "haplotype" refers to a cis arrangement of two or more polymorphic nucleotides, i.e., variances, on a particular chromosome, e.g., in a particular gene. The haplotype preserves the information of the phase of the polymorphic nucleotides—that is, which set of variances was inherited from one parent, and which from the other.

In the context of this invention, the term "analyzing a sequence" refers to determining at least some sequence information about the sequence, e.g., determining the nucleotides present at particular sites in the sequence or determining the base sequence of all of a portion of the particular sequence.

The term "drug" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, lipoproteins, and modifications and combinations thereof. A biological product is preferably a monoclonal or polyclonal antibody or fragment thereof such as a variable chain fragments; cells; or an agent or product arising from recombinant technology, such as, without limitation, a recombinant protein, recombinant vaccine, or DNA construct developed for therapeutic, e.g., human therapeutic, use. The term "drug" may include, without limitation, compounds that are approved for sale as pharmaceutical products by government regulatory agencies (e.g., U.S. Food and Drug Administration (USFDA or FDA), European Medicines Evaluation Agency (EMEA), and a world regulatory body governing the International Conference of Harmonization (ICH) rules and guidelines), compounds that do not require approval by government regulatory agencies, food additives or supplements including compounds commonly characterized as vitamins, natural products, and completely or incompletely characterized mixtures of chemical entities including natural compounds or purified or partially purified natural products. The term "drug" as used herein is synonymous with the terms "medicine", "therapeutic intervention", "pharmaceutical product", or "product". Most preferably the drug is approved by a government agency for treatment of a specific disease or condition.

The terms "disease" or "condition" are commonly recognized in the art and designate the presence of signs and/or symptoms in an individual or patient that are generally recognized as abnormal. Diseases or conditions may be diagnosed and categorized based on pathological changes. Signs may include any objective evidence of a disease such as changes that are evident by physical examination of a patient or the results of diagnostic tests which may include, among others, laboratory tests to determine the presence of variances or variant forms of certain genes in a patient. Symptoms are signs or indications in a patient of a disease, disorder, or condition that differs from normal function, sensation, or appearance, which may include, without limitations, physical disabilities, morbidity, pain, and other changes from the normal condition experienced by an individual. Various diseases or conditions include, but are not limited to, those categorized in standard textbooks of medicine including, without limitation, textbooks of nutrition, allopathic, homeopathic, and osteopathic medicine. In certain aspects of this invention, the disease or condition is selected from the group consisting of the types of diseases listed in standard texts such as Harrison's Principles of Internal Medicine (14th Ed) by Anthony S. Fauci, Eugene Braunwald, Kurt J. Isselbacher, et al. (Editors), McGraw Hill, 1997, or Robbins Pathologic Basis of Disease (6th edition) by Ramzi S. Cotran, Vinay Kumar, Tucker Collins & Stanley L. Robbins, W B Saunders Co., 1998, or other texts described below.

The term "therapy" refers to a process which is intended to produce a beneficial change in the condition of a mammal, e.g., a human, often referred to as a patient. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy can involve, for example, nutritional modifications, administration of radiation, administration of a drug, and combinations of these, among others. Another term that is synonymous with "therapy" is "candidate therapeutic intervention" and is used herein.

In a related aspect, the invention provides a set of computer instructions, which may be a program or set of programs, but is preferably a single program or a set of linked programs that encodes the functions for the method of the preceding aspect.

Preferably the set of computer instructions is embedded in a computer-readable medium, which may be, for example, one or more of read-only memory (ROM), random access memory (RAM), magnetic recording media such as magnetic tape, hard disks, floppy disks, and other magnetic disk formats, as well as in other formats such as optical and magneto-optical disks (e.g., compact disks (CDs) and disks for write-once-read-many (WORM) drives. Preferably, the medium is installed in or is part of a computer system. Such computer systems may be, for example, dedicated purpose computers, general purpose computers, and/or part of a computer network.

Preferably the instruction set is installed in or is part of a general purpose computer which can be part of a network, and also can be connected to a broader network such as the Internet, e.g., for data retrieval. In other embodiments, the instruction set is installed on a computer system in a manner such that the instruction set can be accessed over a network, e.g., over the Internet. In some embodiments, the set of instructions or a necessary part thereof is or can be downloaded from a remote computer over the network, or alternatively can be used for analysis with all or most of the functionality remaining on a storage computer or server. In the latter mode, analysis results can be transmitted to the remote computer.

Thus, the set of instructions for computer-based identification of sequence variances in nucleotide sequences preferably provides sequence comparisons of sets of at least 3 independent sequences of at least portions of a gene; and at least one from a set of filters to distinguish true variances from sequence errors, where execution of the set of instructions on a set of at least 3 independent sequences provides a result indicative of the probability that a sequence difference detected between the sequences in set represents a true variance.

The set of filters preferably includes at least one of: a filter to identify low quality sequence regions, a filter to identify adjacent base changes; a filter to characterize the probability of sequence error or probability of true variance based on sequence context, and a filter utilizing the detection of particular sequence differences at the same sites in multiple sequences as an indication that each such sequence difference represents a true variance. As described in the first aspect, the filters can be used singly or in any combination. The set of filters can also optionally include other filters.

Thus, in related aspects, the invention provides a computer-based or computer-related systems or devices useful for identifying gene sequence variances. Preferably the system is designed to allow access to and utilization of sequence information stored in remote databases.

In one aspect the invention provides a computer readable device that has at least 3 independent nucleotide sequences of at least portions of at least one gene recorded in the device, along with a computer program or programs which analyzes differences between the independent sequences to distinguish true variances from sequence errors.

The device preferably includes a medium selected from floppy disk, computer hard drive, optical disk, computer random access memory, and magnetic tape where the nucleotide sequences or the program or both are recorded on that medium.

As in the above aspects, the program or programs preferably provides functions which include comparing the at least 3 electronic nucleic acid sequences to identify sequence differences between said sequences and at least one of the described filters, which include filters for identifying and removing or discounting sequence differences in portions of the sequences where the number of sequence differences in an analysis window exceeds a predetermined limit; identifying and removing or discounting consecutive mismatches; assigning sequence differences a probability of representing a true variance based on sequence context; and utilizing the detection of particular sequence differences at the same sites in more than multiple sequences as an indication that each such sequence difference represents a true variance. The program or programs can optionally include other functions or filters as well. The result from execution of the program or programs is preferably a score derived from the probability that a detected sequence difference represents a true variance.

In a related aspect, the invention provides a computer-based system for identifying nucleic acid sequence variances. The system includes a data storage medium on which is recorded at least 3 independent nucleotide sequence corresponding to at least portions of at least one gene; a set of instructions allowing analysis of the sequences to identify sequence differences between the independent sequences and to distinguish true variances from sequence errors; and an output device. Preferably the output device is or includes a printer, a video display, and/or a recording medium.

Preferably the set of instructions provides the functions or filters as described in aspects above.

Similarly, in another related aspect, the invention provides a method for identifying nucleic acid sequence variances. The method includes providing a computer-based system for analyzing nucleic acid sequence data, where the system includes a data storage medium in which is recorded at least 3 independent nucleotide sequence corresponding to at least portions of at least one gene, and a set of instructions allowing analysis of said sequences to identify sequence differences between said at least 3 independent sequences and to distinguish true variances from sequence errors; and an output device; analyzing the independent sequences; and outputting results of the analysis to the output device.

Preferably the analysis includes the functions or filters as described in aspects above.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and embodiments of the invention will be apparent from the following description and from the claims.

BRIEF DESCRIPTION OF THE DRAWINGS

FIG. 7 provides exemplary results of analysis using computer-based variance detection, showing alignments of a 100 nucleotide region in the 17-beta-hydroxysteroid dehydrogenase gene, with multiple representatives of the sequence and variances detected using variance scanning. See Example 1 for description of the results.

DETAILED DESCRIPTION OF THE PREFERRED EMBODIMENTS

Figure 1:
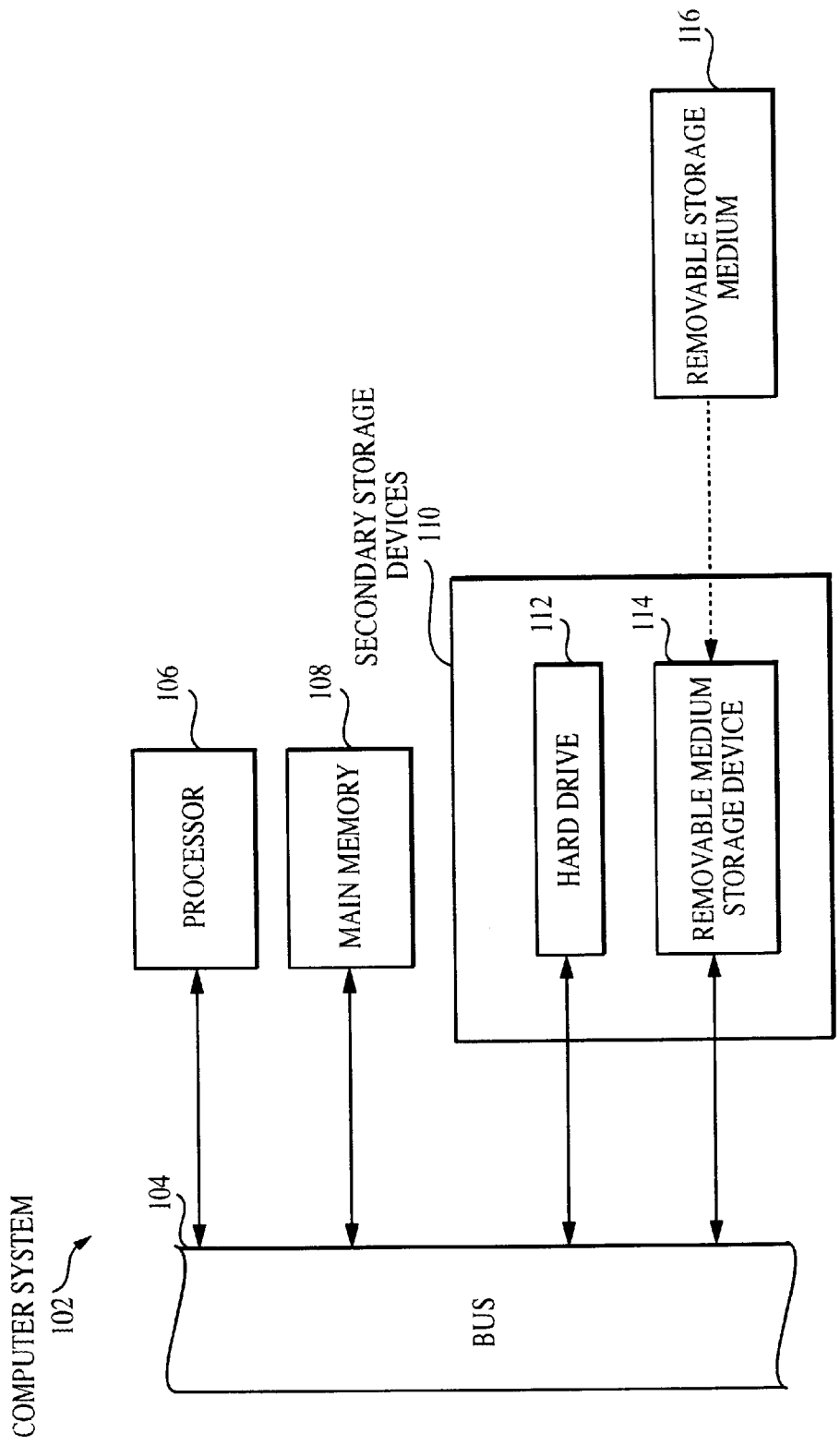
FIG. 1 is a block diagram illustrating a general purpose computer, suitable for use in variance scanning method as described herein.
Figure 2:
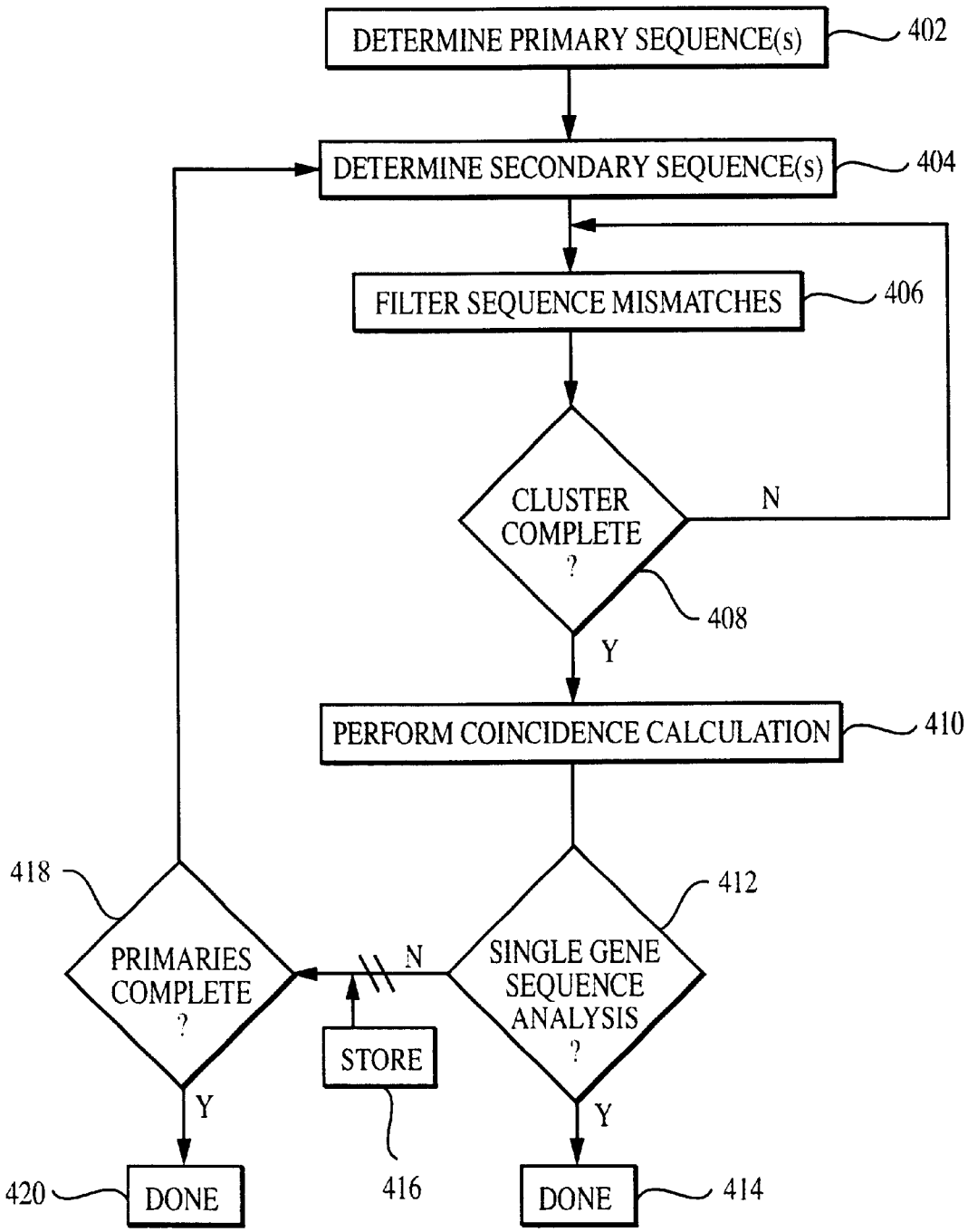
FIG. 2 is flow diagram showing the functions of a variance scanning analysis program as developed in the present invention.
Figure 3:
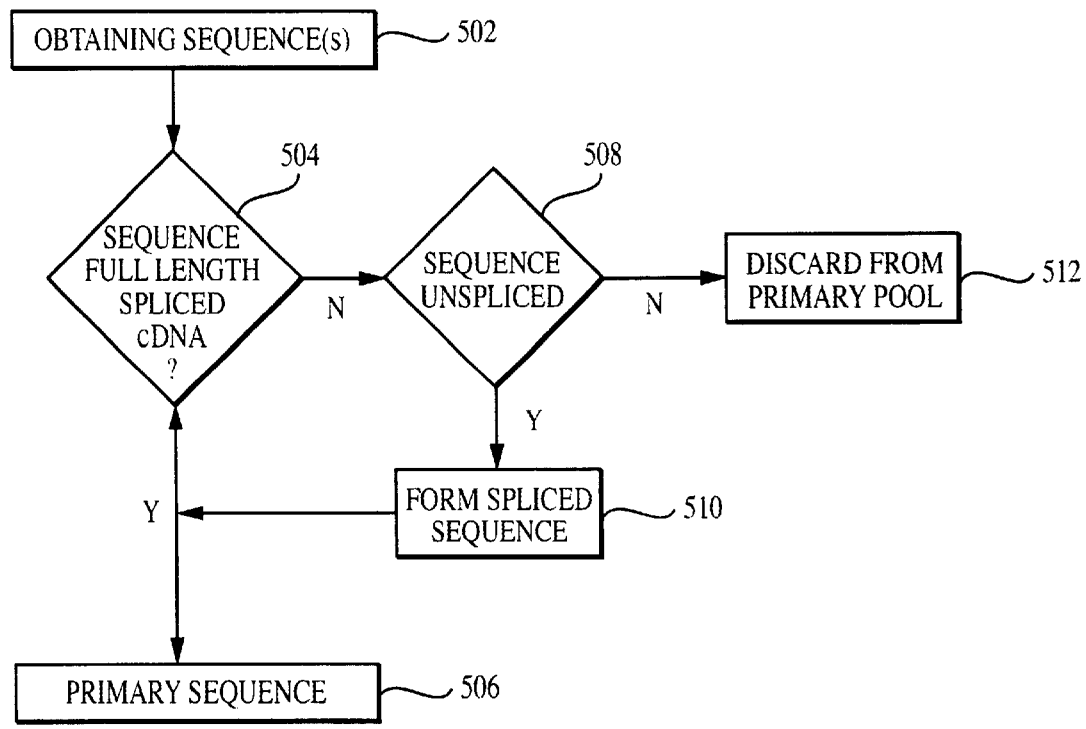
FIG. 3 is flow diagram showing the fundamental steps of determining a primary sequence for use in the process of detecting sequence variances using computer-based analysis.

The identification and confirmation of genetic variances is described in certain patents and patent applications. The description therein is useful in the identification of variances in the present invention. For example, a strategy for the development of anticancer agents having a high therapeutic index is described in Housman, International Application PCT/US/94 08473 and Housman, INHIBITORS OF ALTERNATIVE ALLELES OF GENES ENCODING PROTEINS VITAL FOR CELL VIABILITY OR CELL GROWTH AS A BASIS FOR CANCER THERAPEUTIC AGENTS, U.S. Pat. No. 5,702,890, issued Dec. 30, 1997, which are hereby incorporated by reference in their entireties. Also, a number of gene targets and associated variances are identified in Housman et al., PCT Application-PCT/US98/05419, entitled TARGET ALLELES FOR ALLELE-SPECIFIC DRUGS, filed Mar. 19, 1998, which is hereby incorporated by reference in its entirety, including drawings. Additional variances are described in Stanton et al., U.S. Provisional Appl. No. 60/131,334, filed Apr. 26, 1999, entitled GENE SEQUENCE VARIANCES WITH UTILITY IN DETERMINING THE TREATMENT OF DISEASE, and U.S. patent application, Stanton and Adams, Ser. No. 09/300,747, filed Apr. 26, 1999, entitled GENE SEQUENCE VARIANCES WITH UTILITY IN DETERMINING THE TREATMENT OF DISEASE, which are hereby incorporated by reference in their entireties, including drawings.

1. Screen for Variances in Genes

There are a variety of levels at which a gene can be screened for variances, and a variety of methods for variance screening. The two main levels of variance screening are genomic DNA screening and cDNA screening. Genomic variance detection may include screening the entire segment spanning the transcribed portion of the gene from the transcription start site to the polyadenylation site or a portion of such a complete sequence representing a set of contiguous nucleotides. Alternatively genomic variance detection may (for intron-containing genes) include the exons and some region around them containing the splicing signals, for example. Separate from the issue of scanning introns for variances is the question of screening regulatory DNA sequences for variances. Promoter, enhancer, silencer and other regulatory elements have been described in human genes. Variances in such sequences may affect basal gene expression or regulation of gene expression. In either case, such variation may affect the response of an individual patient to a therapeutic intervention, for example a drug. Thus in practicing the present invention, it is useful to screen regulatory sequences as well as transcribed sequences, in order to identify variances that may affect gene transcription. Frequently information on the genomic sequence of a gene can be found in the sources above, particularly by searching GenBank. The name of the gene can be entered at a site such as Entrez: GenBank sequences can be accessed by connecting a computer to the internet, and searching for NCBI or NLM. Thus, for example, the GenBank sequences are available on the world wide web at the NCBI site, with the remainder of the address being, .nlm.nih.gov/Entrez/nucleotide.html.

Variance detection is often first performed on the cDNA of a gene for several reasons. First, it makes sense that variances in the transcribed portion of a gene are most likely to have functional consequences as they can affect the interaction of the transcript with a wide variety of cellular factors during the complex processes of transcription, processing and translation. Second, as a practical matter the cDNA sequence of a gene is often available before the genomic structure is known, although the reverse may be true in the future. If the genomic structure is not known, then only the cDNA sequence can be scanned for variances.

Although variances within the cDNA are the most likely to have functional consequences, variances identified in other portions of a gene through the use of high-throughput computational method of genomic DNA can provide identification of genetic polymorphisms of significance in relation to drug or therapeutic response in a given disease. For example, SNPs in the promoter, enhancers, silencers or other regulatory sites, introns, splice sites, and 3' untranslated regions of a gene may affect the transcription, translation and message processing of the genetic information thereby affecting protein target levels or concentrations, availability, or activity. Many of these alterations may or may not affect the target protein cellular function. However, these polymorphic differences may have an affect on a drug or therapeutic intervention on a target protein and ultimately affect drug response. Thus, included in these methods are those that can be applied to genomic DNA in order to identify genomic DNA variances. Further, genomic polymorphic differences in the form of SNPs can be markers for functional differences as a result of linkage disequilibrium between the two.

2. Variance Identification and Use

Variance Detection Using Sequence Scanning

In addition to the physical methods of polymorphism detection, e.g., those described above and others known to those skilled in the art (see, e.g., Housman, U.S. Patent No. 5,702,890; Housman et al., U.S. patent application Ser. No. 09/045,053), variances can be detected using computational methods, involving computer comparison of sequences from two or more different biological sources, which can be obtained in various ways, for example from public sequence databases. The term "variance scanning" refers to a process of identifying sequence variances using computer-based comparison and analysis of multiple representations of at least a portion of one or more genes. Computational variance detection involves a process to distinguish true variances from sequencing errors or other artifacts, and thus does not require perfectly accurate sequences. Such scanning can be performed in a variety of ways, preferably, for example, as described below.

The variance scanning method provided by this invention includes functions which involve the acquisition and analysis of multiple sequences for one or more genes. The analysis involves distinguishing actual sequence variances which can be detected in individuals from one or more populations from sequence errors or artifacts which can be introduced, for example, during sequence amplification or sequencing procedures. The output of the analysis provides an indication, for each potential variance detected, whether the potential variance is a true variance or is a sequence error. The indication is preferably provided as a probability measure or other relative scoring result. The process is described generally with reference to FIG. 4.

Typically the process begins by determining a primary sequence 402. The primary sequence serves as a reference sequence for alignments and the following analysis. As recognized by those skilled in the art, such a primary sequence can be selected arbitrarily from a plurality of available sequences, or preferably can be selected to be a high quality sequence if indications of sequence quality are available. Preferably a primary sequence is a full-length cDNA sequence, though partial sequences and full or partial genomic sequences can also be utilized or even assembled clusters or sets of such partial sequences. Two or more partial sequences can be assembled to construct a full-length primary sequence. As recognized by those skilled in the art and as described in more detail below, sequences can be obtained from a variety of sources, including for example, publicly-available or fee-for-access sequence databases and from direct sequencing procedures.

Along with determination of a primary sequence, the process also involves the determination of at least one additional sequence as a secondary sequence or sequences 404. Such secondary sequences can be determined prior to, at the same time as, or subsequent to the determination of a primary sequence or sequences. As the following analysis utilizes sequence comparisons, there will be at least two sequences, one of which will generally be designated as a primary sequence, and the remaining 1,2,3,4,5, 6, 7, 8, 9, 10, or more sequences for a gene can be designated as secondary sequences. For each primary sequence, the corresponding secondary sequences for that gene are analyzed to distinguish or filter sequence mismatches 406. It is clear that the designation of primary and secondary sequences is for convenient reference only. However the sequences are designated, the analysis utilizes 2, preferably 3,4,5, or more sequences corresponding to each gene for which variances are to be identified.

A altering analysis 406 can be implemented in a variety of ways, including the exemplary implementation described in greater detail below. In general, the analysis will include pairwise alignments to detect nucleotide mismatches and analysis of those mismatches to distinguish true sequence variances from sequence errors or other artifacts. Typically, the alignments are performed as pairwise alignments between each secondary sequence and the primary sequence, although other alignments with a set or cluster of sequences corresponding to a gene could likewise be performed and utilized, e.g., multiple alignment. For example, pairwise or multiple sequence alignments could be performed between each independent sequence in a cluster. The detected mismatches could be further analyzed, e.g., as described herein, to distinguish true variances from artifacts.

Following a filter sequences mismatch process, if one or more sequences, e.g., secondary sequences, in a set or cluster remain unanalyzed, then the filter sequences mismatches 406 is performed for each of the remaining sequences in the cluster 408. If analysis of the cluster is complete, then preferably, a coincidence calculation 410 is performed. The results of the coincidence calculation determines a value utilizing the frequency of occurrence of a possible sequence variance in a set of overlapping sequences (e.g., in a sequence cluster) to indicate whether detected mismatches represent true variances. Where this calculation is utilized, putative variances which do not show coincidence are eliminated or assigned a lower probability of being true variances. Preferably the calculation involves assigning a probability or value representing the likelihood that a mismatch in a particular sequence context is a true variance (or a sequence error) along with a weighting based on the frequency of occurrence of the sequence detected as a mismatch in the set of overlapping sequences or sequence cluster. Thus, those mismatches which occur more than once in the set or cluster have correspondingly higher scores (e.g., a higher probability of being a true variance).

If a single gene sequence analysis is being performed 412, then the analysis is done 414. The results can be output, stored, and/or transmitted to any of a variety of programs, databases, or other functional units for further use or preservation. If a single gene sequence analysis is not being performed, but rather a plurality of gene sequences, e.g., cDNA sequences corresponding to a plurality of genes, is being performed, the analysis result or results for the cluster is stored or output 416.

It is also determined whether the primary sequences are complete 418. That is, it is determined whether analysis of the sequence clusters corresponding to each gene to be analyzed is complete. If all primaries (clusters) are not complete, then the process is repeated from determine secondary sequences 404. Once primaries are complete 416, then the analysis is done 420. As with the single gene analysis, the results can be output, stored, and/or transmitted to other functional units.

Collection of Sequences

In accordance with the description above concerning determination of primary sequences 402 and determination of secondary sequences 404 for variance scanning, a plurality of independent sequences for at least a portion of a gene or genes is used for alignment comparison and further analysis. The sequences may be available and/or obtained from any of a variety of different sources. The sequence information may be derived from genomic DNA, cDNA, and/or from RNA. These sequences can be obtained, for example, by original sequencing of nucleic acid from one or more individuals, and/or from one or more sequence databases, preferably publicly available databases such as GenBank and OMIM among others. As indicated, the sequences need not be full-length genes or full-length cDNAs and need not cover identical portions, so long as there is at least one overlap region so that comparisons between sequences covering the overlap regions can be performed.

Figure 5:
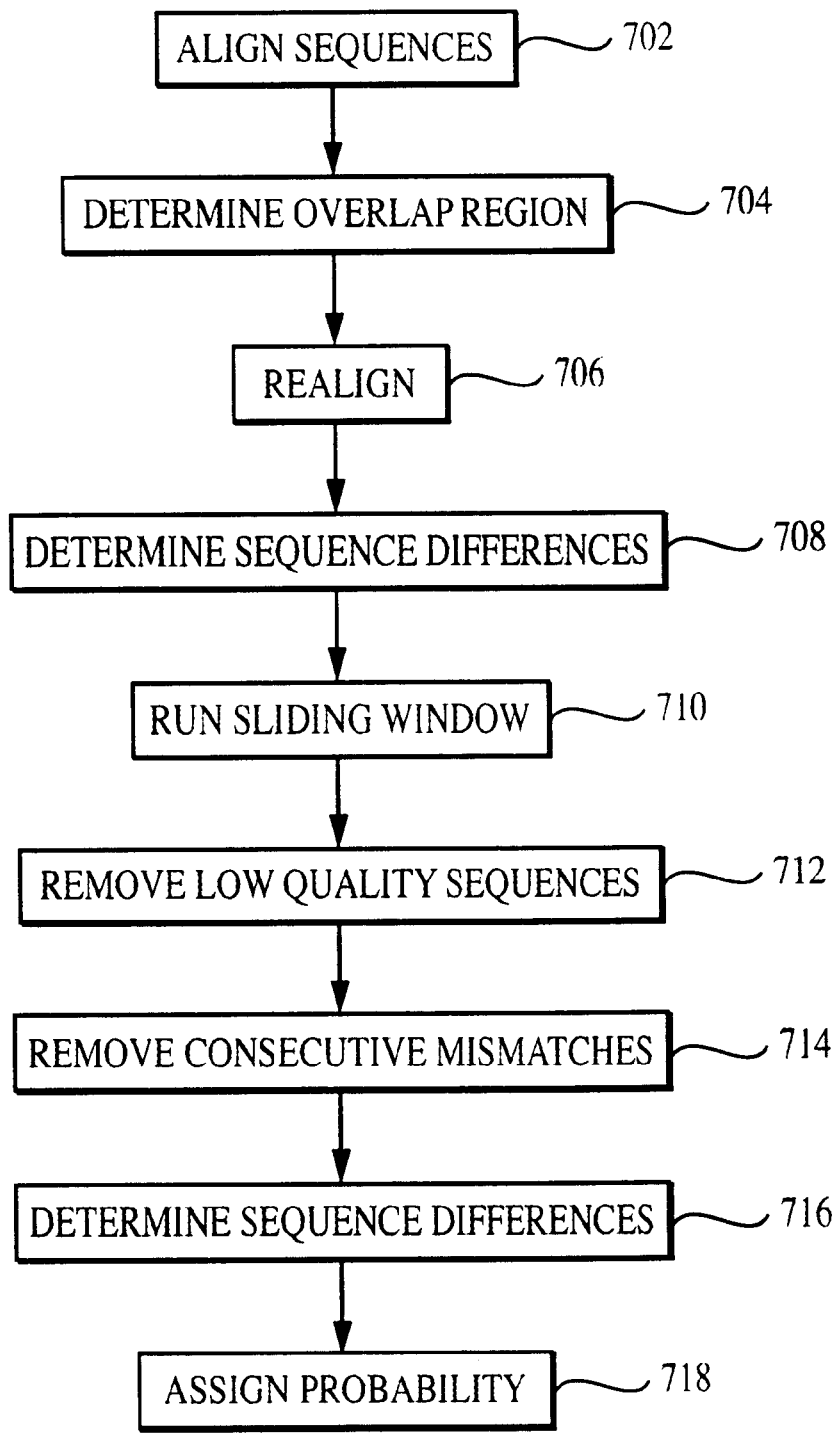
FIG. 5 is a flow diagram showing the fundamental processes in an exemplary embodiment of a computer-based variance detection analysis.

As shown in FIG. 5, generally the determination of a primary sequence or sequences as indicated in 404 of Table 1 involves obtaining or extracting one or more sequences from a sequence database, preferably from a publicly available database such as GenBank, or obtaining or providing a sequence or sequences from another source, e.g., de novo sequencing 502. Preferably at least one full-length cDNA or genomic sequence is obtained 504. The sequence may be complete as originally obtained, including splicing to excise introns and join exons. If such a complete sequence is available, that sequence can be utilized as a primary sequence. If a plurality of complete sequences are available, then generally one is chosen as a primary sequence 506; the remaining sequences can be designated as secondary sequences. As previously indicated, the selection of a primary sequence may be an arbitrary selection or can be based on other factors, such as, for example, known or expected sequence quality. If a sequence is unspliced 508, and the preferred cDNA sequence analysis is to be performed, then the sequence is spliced and exons are joined to form a spliced sequence 510. Multiple partial sequences can be used to construct a longer, preferably complete cDNA sequence. Such splicing can utilize expected or identified splice sites, e.g., splice site information as included with GenBank sequences. Where it is desired to utilize complete cDNA sequences as primary sequences, if a complete, spliced sequence is not available or cannot be constructed from available sequences, then the sequence or sequences are discarded from the primary sequence pool 512.

While the utilization of complete cDNA sequences is highly preferred, it is also possible to utilize genomic sequences. Such analysis may be desired where the detection of variances in or near splice sites is sought. Such sequences may represent fall or partial genomic DNA sequences for a gene or genes. Also, as previously indicated, partial cDNA sequences can also be utilized although this is less preferred. As described below, the variance scanning analysis can simply utilize sequence overlap regions, even from partial sequences. Also, while the present description is provided by reference to DNA, e.g., cDNA, some sequences may be provided as RNA sequences, e.g., mRNA sequences. Such RNA sequences may be converted to the corresponding DNA sequences, or the analysis may use the RNA sequences directly.

As indicated, the acquisition of sequences can be performed variously, the description below is only exemplary. At the present time, multiple representations of cDNAs are available for analysis and the exemplary analysis herein utilizes cDNA sequences.

Acquisition of Drug Target cDNA Sequences

In exemplary variance scanning utilized in the present invention, cDNA sequences were obtained for 449 of the genes listed in Drews and Ryser, 1997 (Drews J and Ryser S, Molecular drug targets and Genomic Sciences 1997, *Nature Biotechnology*: 15:1318–1319), which in turn were largely drawn from Goodman and Gilman (Alfred Goodman Gilman, Joel G. Hardman, Raymond W. Ruddon, Louis Sanford Goodman, Lee E. Limbird, Perry B. Molinoff, eds., *The Pharmacological Basis of Theraputics*, $9^{th}$ Ed., McGraw Hill (1996)) by searching GenBank revision 110 dated December, 1998 (Benson D A, Boguski M S, Lipman D J, Ostell J, Ouellette B F, GenBank, 1998, Nucleic Acids Research 26(1):1–7). In cases where Genbank included several genes which fit a given Drews category, all genes were separately included in the analysis. Where multiple fall-length sequences were available for the same gene, one of these was chosen as the "Primary" sequence. In the present case, the Primary sequence was chosen arbitrarily, but if quality metrics are available, or a sequence is known (e.g., through redundant sequencing) to be of high quality, that sequence is preferably chosen.

Some sequences required post-processing into cDNA format, including the removal of introns, or integration of sequence information from multiple files, e.g., where partial overlapping sequences were obtained. This was achieved with the use of software written for this purpose. Locations of the intron-exon boundaries were contained in the GenBank files, and a simple text-editing script was used to join the indicated exons into a single sequence. The determination of which sequence to use as the Primary sequence was made between multiple instances of the same sequence in a UniGene entry arbitrarily, but could be based on quality metrics if available. Multiple sequences for each of the genes were obtained from UniGene (Build 70)( Schuler G D, Boguski M S, Stewart E A, Stein L D, Gyapay G, Rice K, White R E, Rodriguez-Tome P, Aggarwal A, Bajorek E, Bentolila S, Birren B B, Butler A, Castle A B, Chiannilkulchai N, Chu A, Clee C, Cowles S, Day P J, Dibling T, Drouot N, Dunham I, Duprat S, East C, Hudson T J, et al., 1996, A gene map of the human genome, *Science* 274:540–546). These consist mostly of EST sequences, but contain longer mRNA sequences as well, including, in some cases, alternative fall length cDNA sequences. Only genes for which there was at least one full-length cDNA, a UniGene entry, and at least five sequences in the UniGene family were included in our analysis. A larger number of independent sequences is preferable. The analysis should utilize at least 3 independent sequences, preferably at least 5, more preferably at least 7, still more preferably at least 10.

Acquisition of Full-Length cDNA Sequences cDNA sequences for which sufficient numbers of secondary sequences were available for analysis were obtained for an additional 4659 cDNA sequences, including essentially all of the full-length cDNA sequences present in GenBank. This was accomplished by searching the GenBank revision 110 dated December, 1998 (Benson D A, Boguski M S, Lipman D J, Ostell J, Ouellette B F, GenBank, 1998, *Nucleic Acids Research* 26(1):1–7) for genes annotated as RNA or mRNA. Sequences were determined to be full-length where the GenBank-annotated coding sequence start (CDS) was greater than or equal to the first base of the DNA sequence in the database. Some sequences required post-processing into cDNA format, including the removal of introns, or integration of sequence information from multiple files. This was achieved with the use of software written for this purpose as indicated above, but can similarly be performed using publicly available or commercially-available software which includes such functionality. Multiple sequences for the genes were obtained from UniGene (Build 70) (Schuler, et al., 1996, A gene map of the human genome, *Science* 274:540–546). These consist mostly of EST sequences, but contain longer mRNA sequences as well, including in some cases alternative full length cDNA sequences. Only genes for which at least one fall-length cDNA, a UniGene entry, and at least five sequences in the UniGene family were available were included in our analysis.

Acquisition of additional Gene Fragment Assemblies

EST sequence assemblies were obtained for an additional 11,323 cDNA fragments for analysis from the STACK database (Burke J, Wang H, Hide W, Davison D B, 1998, Alternative gene form discovery and candidate gene selection from gene indexing projects, *Genome Research* 8:276–290). Additional sequences for each gene were also drawn from the assemblies' parent UniGene family (Build 70) (Schuler, et al., 1996, A gene map of the human genome, *Science* 274:540–546). These family members consist only of EST and fragmentary sequences. Only genes for which at least five sequences in the UniGene family were available were included in our analysis. Similarly, ESTs or other gene or cDNA fragments can also be used in variance scanning analysis.

Computational Variance Detection

In an exemplary embodiment, variances were discovered with the use of a computer program implementation, which uses an analysis as described below. The analysis can be implemented in many different particular ways. Thus, a variety of different implementations can be utilized which distinguish variances from sequencing errors. Preferably, such other software includes at least some of the types of sub-analyses or filters as described below for the exemplary implementation. As recognized by those skilled in the art, such analysis software may be implemented in many different ways, using any of a variety of different programming languages, and for a variety of different computer platforms. Thus, the present description is provided in general terms rather than with the details of the specific implementation. As recognized by those skilled in the art, analyses, e.g., the present variance scanning analysis, can be structured in many different ways, including, for example, a set of independent programs which each perform a portion of the analysis. Such programs may function independently, e.g., with each program being initiated by the operator or operators, or one or more of the programs may call a succeeding program or programs, and may also pass data to succeeding programs. In other alternatives, a single program can be constructed which can, for example, be a single block of integrated code, or can be a modular or object-oriented program or various combinations.

Figure 4:
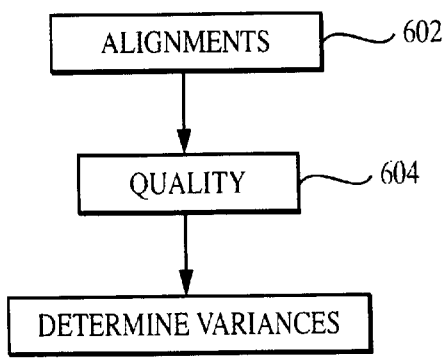
FIG. 4 is a flow diagram showing the fundamental analysis processes utilized in an embodiment of the present computer-based variance detection analysis.
Figure 6:
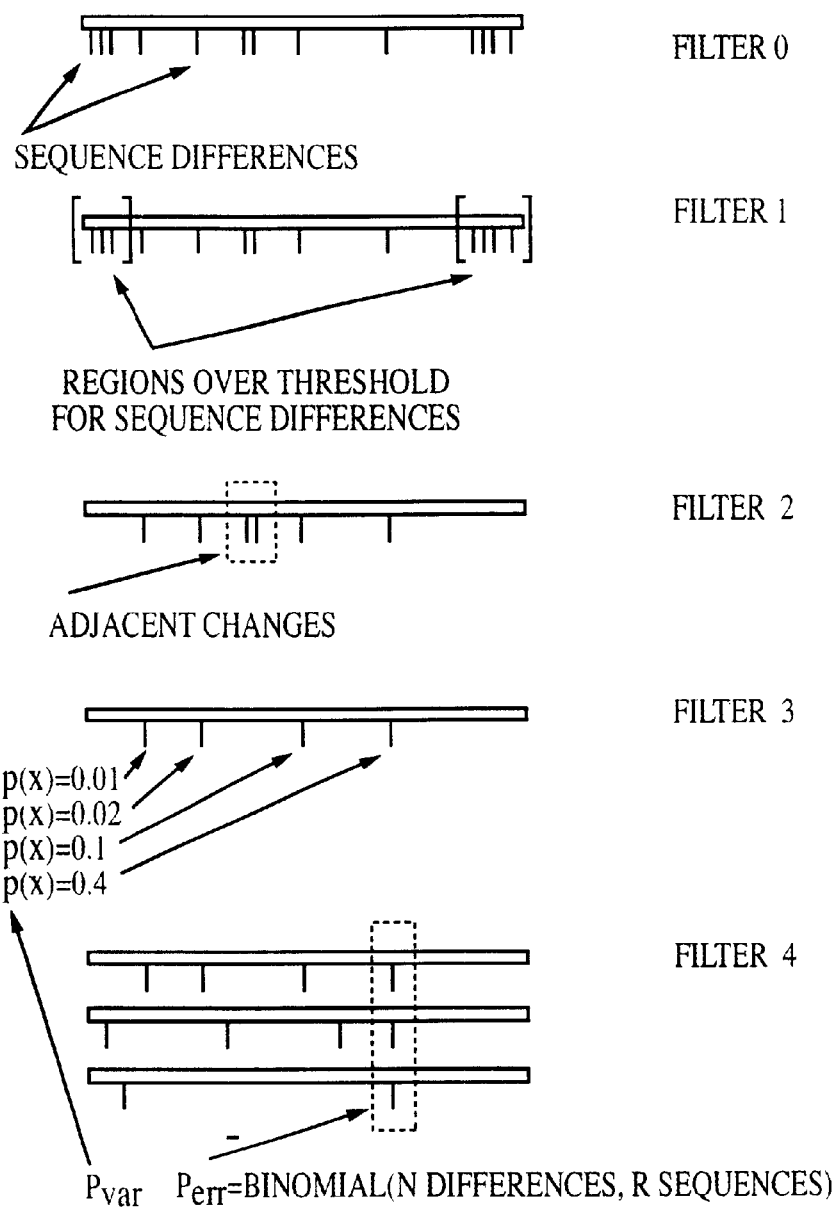
FIG. 6 is a schematic diagram showing an exemplary computer-based filtering process to identify true sequence variances.

A general process for the filter sequence mismatches 406 process shown in FIG. 4 is shown in FIG. 6. The process involves aligning sequences from a gene cluster, generally pairwise alignments 602 between a primary sequence and each secondary sequence, identifying overlap regions and mismatches. Except in cases where sequences are known to be of high quality, it is highly preferably to trim sequences to eliminate low quality portions or to eliminate entire sequences which appear to be of excessively low quality 604. The mismatches in sequences to be firer analyzed are evaluated to determine true sequence variances 606. While such evaluation can be performed in many different ways, the process generally utilizes relationships in sequences which are indicative of sequencing errors or indicative of true sequence variances to identify mismatches which are identified as true variances. It can also make use of external sequence quality measures, such as chromatograms or quality scores to evaluate mismatches.

The process is shown in more detail in FIG. 7. As described in the previous figure, pairwise sequence alignments 702 are performed to identify overlap regions 704. Typically, this alignment utilizes conventional constants for match/mismatch and gap insertion/extension. The alignment can utilize any of a variety of different alignment algorithms or programs, e.g., Smith-Waterman, BLAST, FASTA, SEQUENCHER, and others that are available or are later developed. While it is possible to utilize the mismatches identified in this initial alignment directly, preferably the overlap region is re-aligned 706, preferably with match/mismatch and gap insertion/extension parameters adjusted to weight short insertions or deletions (indels) versus multiple mismatches in a more biologically realistic manner. Those skilled in the art are familiar with such alignment parameter adjustments and how to set such adjustments. The sequence differences are determined from the re-alignment 706. The sequence differences can be identified in any of a variety of formats, e.g., as string edits.

The sequences are analyzed to remove sequences and variances that would be likely to introduce error into the variance identification. Low quality sequences or the mismatches associated with low quality sequence regions are removed, or assigned a low probability of being a true variance. Preferably the analysis is designed to remove low quality sequence ends. Preferably, low quality sequence regions are identified by using a window of a specified length run over the overlap region sequence 710. While the window can be set to any desired length, typically the window is 5, 10, 20, 40, 50, 80, or 100 nucleotides in length. The criterion for inclusion of a mismatch is based on the level of mismatches initially identified for the window region. Preferably the allowable level of mismatches is no more than I mismatch in 10 nucleotides, but can also be set to other levels as desired. Based on the inclusion criterion, mismatches or the sequences which contain those mismatches are retained or removed 712 from the variance list (or assigned a lower probability of being a true variance). Preferably the window system is used to identify the longest region of the overlap which satisfies the mismatch level criterion, and mismatches within that longest region are utilized. A quality filter may be applied in other ways. For example, a window around each identified mismatch may be used, where the level of mismatch within the window does not exceed a defined level. For example, a 10-, 20- or 30-nucleotide window can be used, with 0, 1, 2, or 3 mismatches allowed in addition to the particular initial mismatch. Where a higher level of mismatches is observed within the window, the mismatches can be discarded or discounted as previously described. In addition, it is known that sequence quality is often significantly poorer near the end of a sequenced fragment. Therefore, even if an excessive number of mismatches is not observed in an end or ends of an alignment match, preferably the ends of the match are trimmed, e.g., by 5, 10, or 20 nucleotides, to eliminate mismatches in those regions from the list of putative variances (or discount the probability of mismatches in those regions representing true variances).

In addition to the sequence quality evaluation, preferably the quality determination also includes identification and removal (or probability discounting) of consecutive mismatches 714. This filter is biologically reasonable, because the occurrence of adjacent nucleotide mutations is known to be very rare. Therefore, it is highly likely that at least one (and often both) of the adjacent mismatches is an artifact. Therefore, preferably the adjacent mismatches are removed from the list of variances. However, if other factors are present to indicate that one or both of the adjacent mismatches represent real sequence variance (e.g., due to confirmation of the sequences being compared and/or the coincidence of the variant nucleotide or nucleotides creating the mismatches in a number of different, independently derived sequences, this filter can be relaxed (e.g., using adjustments to probabilities) or eliminated.

The sequence differences 716 following the sequence quality and/or dinucleotide removal filters are preferably analyzed in their sequence context. This analysis results in a measure indicating whether each sequence difference represents a true variance or a sequence error or artifact. Preferably each sequence difference is assigned a probability 718 based on the likelihood of it representing a real sequence variance. This probability can be derived in many different ways, any of which can be utilized in this invention. For example, in preferred embodiments, the probability or measure indicating the likelihood that the sequence variance is a true variance is based on comparisons of the probability of a sequence error occurring in a particular sequence context versus the probability of a mutation occurring in a particular sequence context. The probability of sequence error can be obtained or estimated from large numbers of sequencing results, preferably such that essentially all local sequence contexts have been or can be analyzed for sequence error. The probability of mutation can be obtained or estimated, for example, by reviewing the sequence contexts of known variations, and/or the contexts of mutations occurring in response to mutagenizing agents or conditions. The weighting of variables in the calculation can be empirically adjusted through experience or confirmatory data, e.g., sequence confirmations using redundant sequencing. Variances which are more likely to represent systematic sequencing errors are eliminated or assigned a lower probability of being true variances, while those detected variances which are in a sequence context which is more likely to represent a mutation are retained and are preferably assigned a higher probability of representing a true variance.

An exemplary program embodiment was implemented as a modular object-oriented system, written in a combination of Python, C/C++, and Java. The system was run on a SGI Origin2000 with 4 processors and 1GB of RAM. Sequences were stored in a relational database schema built on Oracle software. As indicated, many different specific implementations could be used, including, for example, different programming languages, different program structure and/or data structures for code or result data, different hardware, and different output modes or output presentations.

Algorithm

The algorithm for variance discovery was implemented as a series of filters, each successively applied to the output of the last. Other designs could be utilized, for example, certain filters could be combined, or other filters could be utilized.

---

Alignment (Filter 0) Pseudocode

---

```
For each primary:
    For each secondary:
        match = smith_waterman_align(primary, secondary, match=10,
            mismatch=-9,open_gap=-50, extend_gap=-3)
        trim(primary, match.primary_start,
match.primary_end)
        trim(secondary, match.secondary_start,
match.secondary_end)
        match = smith_waterman_align(primary, secondary, match=10,
            mismatch=-9,open_gap=-15, extend_gap=-1)
        mutations = get_mut(match)
        save to database( mutations )
```

---

Alignment (Filter 0)

The listing above provides exemplary pseudocode to implement an alignment of primary and secondary sequences. Pairwise alignment was performed between the "primary" full-length cDNA sequences and each of the "secondary" sequences (e.g., ESTs) using an implementation of the algorithm of Smith and Waterman (Smith T F, Waterman M S, 1981, Comparison of Biosequences, *Adv. Appl. Math.* 2:482–489). This implementation used a two-pass method, first aligning the sequences using conventional match scores for the first pass (match score=10, mismatch penalty=9, gap insertion penalty=50, gap extension penalty=3), which reliably identifies the region of overlap between these sequences, and then a realignment of this overlap using relaxed gap insertion and extension penalties (15 and 1, respectively), to weigh short indels relative to multiple mismatches more realistically. The differences between the two sequences, expressed as string edits in the form of mismatches, insertions, and deletions, were transmitted to the remaining filters.

Other alignment methods for Filter 0 can, for example, include pairwise multiple alignment, hidden-Markov models, and pairwise alignment using other alignment algorithms, such as BLAST and FASTA. The constants which define the alignment parameters may be adjusted, or the number of alignments per pair may be increased using different parameters, or even different alignment methods. Back-propagation optimization, or other similar techniques may be used to further optimize these parameters against specific data sets. The intermediate representation of the results can take the form of a large array, each cell of which contains the nucleotide base (or inserted gap, if appropriate) for the given sequence at the given position. An array may also be used which simply represents the observed frequency of nucleotide observations at that position (Gribskov M, McLachlan A D, Eisenberg D, Profile analysis: detection of distantly related proteins, 1987, PNAS (USA): 4355–4358), yielding some unique mathematical properties to the alignment. Other methods with similar utility include small ungapped alignments (BLOCKS (Henikoff S, and Henikoff J G, 1991, Automated assembly of protein blocks for database searching, Nucleic Acids Research 19(23) :6565–6572)) and hidden Markov models (Eddy S, 1996, Hidden Markov Models, Current Opinion in Structural Biology 6:316–365).

---

Quality Window (Filter 1) Pseudocode

---

```
for each secondary:
    secondary.quality_start = secondary.primary_start + 10
    secondary.quality_end = secondary.primary_end - 10
    while there is a mutation at secondary.quality_start
begin:
        secondary.quality_start = secondary.quality_start +1
    end while
    while there is a mutation at secondary.quality_end
begin:
        secondary.quality_end = secondary.quality_end - 1
    end while
    endpoints = array of ( quality_start, mutations
between,
                            quality_end )
    quality_start = first endpoint
    quality_end   = last endpoint
    longest_region = -2 /* smaller than any possible
result */
    for each endpoint up until 5 from the end:
        /* find the start of a quality region */
        for endpoint from where we left off until 5 from
the end:
            if(distance between this endpoint and the one 5
later<= 50 ):
                move down one endpoint
            else:
                quality_start = (the endpoint 5 later) + 1
                exit loop
        /* find the end of a quality region */
        for endpoint from where we left off until 5 from
the end:
            if(distance between this endpoint and the one 5
later<= 50 ):
                quality_end = (this endpoint) - 1
                exit loop
        /* is this the longest quality region so far? */
        if( (quality_end - quality_start) > longest_region
            secondary.quality_start = quality_start
            secondary.quality_end   = quality_end
            longest_region = quality_end - quality_start
        if ( secondary.quality_end - secondary.quality_start
< 50 ) then:
            mark secondary as unuseable
```

---

Quality Window (Filter 1)

The listing above provides pseudocode for an exemplary implementation of a sequence quality filter, which eliminates mismatches as potential sequence variances (or eliminates entire sequences) where the sequence portion in which the mismatches are found is, or is believed to be, of low quality. The designation of low quality sequence can be adjusted as desired, e.g., to optimize the balance between number of variances identified and the possibility of identifying a variance which is actually an artifact.

Sequencing errors are more common at the ends of sequences, and some sequences contain an excessive numbers of errors. Therefore, it is generally useful to remove sequences expected to contain high levels of sequencing errors from the subsequent analysis. Thus, to farther improve the quality of the sequence fed to later stages of the program, a quality window filter is preferably applied. In the present scanning analysis, Primary/Secondary alignments were scanned with a 50 bp window for the longest contiguous segment with less than 5 differences in 50 bases. This acted to remove low-quality sequence ends, and, for very error-filled sequences, the entire sequence. We found that even where an excessive number of errors were absent, differences observed at the ends of the alignment were nonetheless unreliable. Thus, all matches were trimmed by at least 10 bp if the windowed quality filter did not remove that much at minimum.

This filter may be altered in a variety of ways as desired, e.g., to increase processing speed and/or discrimination. For example, the window may be selected to be of different lengths, e.g., 20, 30, 40, 50, 60, 80, or 100 base lengths, between the specified lengths, or lengths longer than those specified. The discrimination may also be made more relaxed or more stringent. For example, while the above specified less than 5 differences in 50 bases (a rate of legs than 1 in 10) the rate could also be 0.5 in 10 or less, 1.5 in 10 or less, or 2 in 10 or less, among others. The discrimination level can be adjusted depending on available information. For example, if the primary sequence is known to be of high quality, the stringency of the discrimination could be increased to select high quality comparison sequences. Alternatively, the stringency of the discrimination could be decreased to maximize, or increase, the number of putative variances passed to subsequent filters. Those skilled in the art readily recognize the parameters for this filter and how they affect the output, and can readily optimize those parameters.

This filter is heuristic, with values which may be optimized by back-propagation. The filter could be replaced by other, more detailed analysis of sequence quality, particularly in cases where definitive sequence quality measures for each base are present. In cases where the sequence chromatograms are available, similar measure could be derived directly from this source.

---

Adjacency (Filter 2) Pseudocode

--- for each secondary:
    for each mutation in this secondary:
        if( (the mutation is a basechange) AND
            ((there exists a mutation in this secondary at position - 1)
            OR
            (there exists a mutation in this secondary at position+1))):
            mark the mutation as unuseable

---

Adjacency Filter (Filter 2)

Some two-base consecutive base changes are detected despite the previous two filters. This is a biologically unlikely situation which cross-validation showed to be a source of error, and which is preferably removed from further analysis. Filter 2 removed both consecutive mutations by processing the list of observed sequence differences and removing those which occur in adjacent sequence positions. Although this filter seems arbitrary, it has both theoretical validity and strong experimental support.

Adjustments in the alignment system or the aligned sequence representation can replace this filter, with the relationships between adjacent variances represented mathematically. In fact this filter could be dynamically applied based on the context of the surrounding sequence, or even on the values of the quality scores if available.

---

Dinucleotide Frequency (Filter 3) Pseudocode

--- for each useable secondary:
    for each useable basechange mutation of this secondary:
        retrieve from primary( the normal base at this position and
            the preceding base at this position)
        look up in table( 1) p_error: the probability that this dinucleotide would have a sequencing
            error to the mutant base.
        2) p_mut: the probability that there would
            be a natural mutation at this dinucleotide to this base.
    store these values in the mutation

---

Dinucleotide Frequency (Filter 3)

Once the mutations have been screened with the quality filters, the process of building probability models was begun. Not all sequences are equally likely to be the sites of either sequencing errors or of variances. This filter can be implemented in various ways. In the present implementation, Filter 3 takes advantage of the fact that the probability of sequencing error and variance at a given dinucleotide vary. In this analysis, the dinucleotide consisting of the differing base and the base one position immediately upstream were considered. The probability of variance for each of the three possible changes at each of the 16 possible dinucleotides was estimated from the frequency of detection of those base changes at those dinucleotides in human mutations (Cooper, D. N. and Krawczak, M. "Human Gene Mutation" page 139, BIOS Scientific Publishers Limited, Oxford 1993). Similarly, the probability of sequencing error was estimated from the frequency of occurrence of sequencing errors by the overall frequency of differences observed in our data set. This second estimate works because sequencing errors are about 10 times more common than variances. These occurrence frequencies were utilized by processing through the difference list, and generating a pair of frequencies for each difference based on the source sequence (two upstream bases for dinucleotide frequencies) at that position. One frequency context drawn from a table generated with mutation data, and one drawn from a table generated from sequencing error. A data structure with this data for each remaining sequence differences was passed to the final filter as the basis for generation of a score for variance validity Additionally, we have used larger nucleotide word sizes. Hexanucleotide tables containing sequence changes in a 6-nucleotide context rather than the 2-nucleotide context as above have been used. This yields greater distinguishability between variances and sequencing errors to give a good balance of quality and processing time, with the word size still small enough to allow a dense matrix from the available sequence information. Other sequence context-derived systems may be used, such as regular-expression- or profile-based storage of common sequencing errors or mutations (Adams R M, Das S, Smith T F, 1996, Multiple domain protein diagnostic patterns, Protein Science 5:1240–1249; Smith R, Smith T, 1992, Pattern-induced multi-sequence alignment (PIMA) algorithm employing secondary-structure-dependent gap penalties for use in comparative protein modeling, Protein Engineering, 5:35–41). A hash table or binary tree can give a flexible and space-efficient storage data structure for this data, while yielding unique computational properties for calculation of probabilities.

| Coincidence (Filter 4) Pseudocode |
| --- |
| for each useable secondary:<br>    for each useable basechange mutation of this secondary:<br>        use mutation if it is within quality region of this secondary<br>    for each position in mutations where there is a mutation:<br>        /* note that p_error and p_mut for all these mutations is<br>        the same*/<br>        for each useable secondary:<br>            n_sites = n_sites + 1 if position is within quality region<br>            n_muts = number of mutations at this position<br>            p_n_errors = binomial (n_muts, n_sites, p_error)<br>            p_variance = p_mut / (p_mut + p_n_errors) |

Coincidence (Filter 4)

Variances are expected to be detected at the same site in multiple sequences, whereas sequencing errors should be so detected relatively rarely. The final filter uses this characteristic to distinguish between sequencing errors and variances. The probability that the observed differences at a given site represented a variance ($P_{var}$) was assigned the value obtained from Filter 3. Using the probability from Filter 3 (P), the aggregate probability that the N observed differences in the R sequences were due to coincident sequencing errors ($P_{err}$) was calculated using the binomial distribution for N successes in R trials where P is the probability of a success. A score that there was, in fact, a variance at that site in the gene sequences was calculated as:

$$POFVAR = P_{var}/(P_{var}+P_{err})$$

Sites where this score was greater or equal to 0.2 were predicted as sites of variances.

Obviously, the cutoff score is a variable which can be optimized by crossvalidation, possibly for specific data subsets as determined by heuristics based on other information in the database. The mathematical models used are easily understandable, and the results can be improved with the addition of more comprehensive methods.

In addition, the restrictiveness of the various filters can be individually adjusted based both on validation work, and can also be adjusted depending on the type of result desired. For example, if it is desirable for a particular application to detect a higher fraction of variances, and a larger false positive rate is acceptable, particular filters can be relaxed or even eliminated to provide an appropriate balance between detection and probability of a detected variance representing a true variance. On the other hand, if it is more desirable to ensure that the detected variances retained have a very high probability of representing true variances and it is acceptable to reject many detected variances which actually correspond to true variances, then one or more filters can be made more restrictive and/or addition filters can be added. Adjustments of this type can be based on validation experiments and/or other empirical factors.

Computer System Implementation

The variance scanning system as described above is generally embedded or stored in a computer hardware system. Such a system is arranged to have a device or devices for entering data and/or commands, one or more storage or memory devices or components, one or more processing systems, and one more output devices. The components are interconnected so that sequence analyses can be initiated and controlled, sequence data can be obtained or retrieved, and output can be observed and/or recorded. The system may be, for example, a stand-alone computer, a computer connected to a network, or a terminal attached to a network. Thus, the invention provides a computer system with all or part of a variance scanning software system as described above embedded therein. Sequence data for analysis may also be recorded in storage media or may be retrieved from a remote location or locations. Typically, such data would be at least temporarily stored in the computer system. Also at least temporarily stored in the computer system will be at least a portion of the analysis instructions so that at least a portion of the described analysis can be performed using the sequence data. Depending on the program structure, the analysis instructions can be called or loaded in various ways. For example the analysis instructions can be called in portions as needed, all of the instructions for an analysis can be loaded at one time, or analysis with one program can be completed and the result data stored before a further program is loaded for additional analysis.

3. Analysis of Haplotypes Increases Power of Genetic Analysis

Usually, variation in activity due to a single gene or a single genetic variance in a single gene is not sufficient to account for observed variation in patient response to a treatment, e.g., a drug, there are often other factors that account for some of the variation in patient response. This is to be expected as drug response phenotypes usually vary continuously, and such (quantitative) traits are typically influenced by a number of genes (Falconer and Mackay, 1997). Although it is impossible to determine a priori the number of genes influencing a quantitative trait, often only a few loci have large effects, where a large effect is 5–20% of total variation in the phenotype (Mackay, 1995).

The sequential testing for correlation between phenotypes of interest and single nucleotide polymorphisms may be adequate to detect associations if there are major effects associated with single nucleotide changes; certainly it is useful to this type of analysis. However there is no way to know in advance whether there are major phenotypic effects associated with single nucleotide changes and, even if there are, there is no way to be sure that the salient variance has been identified by screening cDNAs. A more powerful way to address the question of genotype-phenotype correlation is to assort genotypes into haplotypes. Haplotype analysis has several advantages compared to the serial analysis of individual polymorphisms at a locus with multiple polymorphic sites.

(1) Of all the possible haplotypes at a locus ($2^n$ haplotypes are theoretically possible at a locus with n binary polymorphic sites) only a small fraction will generally occur at a significant frequency in human populations. Thus, association studies of haplotypes and phenotypes will involve testing fewer hypotheses. As a result there is a smaller probability of Type I errors, that is, false inferences that a particular variant is associated with a given phenotype.

(2) The biological effect of each variance at a locus may be different both in magnitude and direction. For example, a polymorphism in the 5' UTR may affect translational efficiency, a coding sequence polymorphism may affect protein activity, a polymorphism in the 3' UTR may affect mRNA folding and half life, and so on. Further, there may be interactions between variances: two neighboring polymorphic amino acids in the same domain—say cys/arg at residue 29 and met/val at residue 166—may, when combined in one sequence, for example, 29cys-166val, have a deleterious effect, whereas 29cys-166met, 29arg-166met and 29arg-166val proteins may be nearly equal in activity. Haplotype analysis is the best method for assessing the interaction of variances at a locus.

(3) Templeton and colleagues have developed powerful methods for assorting haplotypes and analyzing haplotype/phenotype associations (Templeton et al., 1987). Alleles which share common ancestry are arranged into a tree structure (cladogram) according to their time of origin in a population. Haplotypes that are evolutionarily ancient will be at the center of the branching structure and new ones (reflecting recent mutations) will be represented at the periphery, with the links representing intermediate steps in evolution. The cladogram defines which haplotype-phenotype association tests should be performed to most efficiently exploit the available degrees of freedom, focusing attention on those comparisons most likely to define functionally different haplotypes (Haviland et al., 1995). This type of analysis has been used to define interactions between heart disease and the apolipoprotein gene cluster (Haviland et al 1995) and Alzheimer's Disease and the Apo-E locus (Templeton 1995) among other studies, using populations as small as 50 to 100 individuals. The goal of haplotyping will be to identify the common haplotypes at selected loci that have multiple sites of variance.

4. Comparison of this Computational Method with Others

Recent work describing computational SNP detection has included methods which utilize sequence quality filters. Among the differences, our methods significantly differ in at least two important areas. In the first, alignment methodology as described above makes use of two iterations of pairwise local (Smith-Waterman) alignment, each with different scoring parameters. In the paper by Picoult-Newberg et al., PHRAP was used to assemble the sequences, which itself uses a Smith-Waterman based single-pass multiple alignment method. Buetow et al. in used single-pass PHRAP alignment, but in addition were dependent on the quality scores drawn from the automated sequencing process, an analysis this method does not require. The second difference is scoring methodology. This invention makes use of a method based on binomial statistics and the probability of nucleotide variation for short nucleotide words, while Buetow et al. use standard Bayesian methods for predicting nucleotide heterogeneity.

EXAMPLES

Examples 1 and 2 below present exemplary genes where genetic variances have been identified using the computational methods as described in the Detailed Description.

Example 1

Variance Scanning

An exemplary variance scanning result is shown in FIG. 7 for a portion of the 17-beta-hydroxysteroid dehydrogenase gene. The figure shows a 100 nucleotide region in the 17-beta-hydroxysteroid dehydrogenase gene (GenBank X87176, the primary sequence at the top) and aligned associated UniGone cluster members. The alignment is the result of iterative pairwise single alignments between the cluster members and the anchoring primary sequence (top) via the Smith/Waterman local alignment algorithm. The differences observed in the aligned sequences without filtration is shown in the line second from the bottom, labeled "Tot.Obs.Var." At the bottom of the figure, the line labeled "After Filter" indicates the variances which remain after all filtration stages are complete. Note that almost all of the observed differences are filtered out, presumably present due to sequencing error.

The sequences were obtained and the variance scanning was performed as described above.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other coding language; and/or computational methods is within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

What we claim is:

1. A method for identifying at least one variance in at least one gene, comprising:

for a selected gene, providing at least three independent nucleic acid, sequences with sequence overlap regions, wherein the sequences are on a computer readable medium;

comparing the sequence overlap regions to identify sequence differences; and analyzing the sequences or the sequence differences or both to discriminate sequencing errors from sequence variances for the selected gene, the analyzing step comprising identifying and discounting consecutive mismatches, the analyzing step further comprising at least one of:
  (i) identifying and discounting sequence differences in portions of the sequences wherein the number of sequence differences in a selected analysis window exceeds a predetermined limit; and
  (ii) utilizing the detection of particular sequence differences at the same sites in multiple sequences as an indication that each such sequence difference represents a true variance.

2. The method of claim 1, wherein the analyzing step further comprises:
  assigning sequence differences a probability of representing a true variance based on sequence context wherein the result is a score derived from the probability that a detected sequence difference represents a true variance.

3. The method of claim 1, wherein the analyzing step comprises:
  identifying and discounting sequence differences in portions of the sequences wherein the number of sequence differences in a selected analysis window exceeds a predetermined limit.

4. The method of claim 1, wherein the analyzing step further comprises assigning sequence differences a probability of representing a true variance based on sequence context.

5. The method of claim 1, wherein the analyzing step comprises
  utilizing the detection of particular sequence differences at the same sites in multiple sequences as an indication that each such sequence difference represents a true variance.

6. The method of claim 1, wherein the analyzing step comprises
  identifying and discounting sequence differences in portions of the sequences wherein the number of sequence differences in an analysis window exceeds a predetermined limit, and
  assigning sequence differences a probability of representing a true variance based on sequence context.

7. The method of claim 1, wherein the analyzing step comprises
  identifying and discounting sequence differences in portions of the sequences wherein the number of sequence differences in an analysis window exceeds a predetermined limit, and
  utilizing the detection of particular sequence differences at the same sites in multiple sequences as an indication that each such sequence difference represents a true variance.

8. The method of claim 1, wherein the analyzing step comprises
  assigning sequence differences a probability of representing a true variance based on sequence context; and
  utilizing the detection of particular sequence differences at the same sites in multiple sequences as an indication that each such sequence difference represents a true variance.

9. The method of claim 1, wherein the analyzing step comprises
  identifying and discounting sequence differences in portions of the sequences wherein the number of sequence differences in a selected analysis window exceeds a predetermined limit;
  assigning sequence differences a probability of representing a true variance based on sequence context; and
  utilizing the detection of particular sequence differences at the same sites in multiple sequences as an indication that each such sequence difference represents a true variance,
    wherein the result is a score is derived from the probability that a detected sequence difference represents a true variance.

10. A computer readable device having recorded therein at least three independent nucleic acid sequences of at least portions of at least one gene; and
  a computer program or programs which analyzes differences between the at least three independent sequences to distinguish true variances from sequence errors,
    wherein the program or programs provides the functions of
    comparing the at least three sequences to identify sequence differences between the sequences;
    identifying and discounting sequence differences in portions of the sequences wherein the number of sequence differences in an analysis window exceeds a predetermined limit;
    identifying and discounting sequence differences that are part of consecutive mismatches;
    assigning sequence differences a probability of representing a true variance based on sequence context; and
    utilizing the detection of particular sequence differences at the same sites in multiple sequences as an indication that each sequence difference represents a true variance,
      wherein the result is a score is derived from the probability that a detected sequence difference represents a true variance.

11. The device of claim 10, wherein the at least three independent sequences is at least five independent sequences.

12. The device of claim 10, wherein the device comprises a medium selected from the group consisting of floppy disk, computer hard drive, optical disk, computer random access memory, and magnetic tape wherein the nucleotide sequences or the program or both are recorded on the medium.

13. A computer-based system for identifying nucleic acid sequence variances, comprising:
  a) a data storage medium having recorded thereon at least three independent nucleic acid sequences corresponding to at least portions of at least one gene;
  b) a set of instructions allowing analysis of the sequences to identify sequence differences between the at least three independent sequences and to distinguish true variances from sequence errors,
    wherein the set of instructions provides the functions of:
    comparing the at least three sequences to identify sequence differences between the sequences;
    identifying and discounting sequence differences in portions of the sequences wherein the number of sequence differences in a selected analysis window exceeds a predetermined limit identifying and discounting sequence differences that are part of consecutive mismatches;

assigning sequence differences a probability of representing a true variance based on sequence context, and utilizing the detection of particular sequence differences at the same sites in multiple sequences as an indication that each such sequence difference represents a true variance, wherein the result is a score derived from the probability that a detected sequence difference represents a true variance; and c) an output device.

14. The system of claim 13, wherein the output device comprises a device selected from the group consisting of a printer, a video display, and a recording medium.

15. A method for identifying nucleic acid sequence variances, comprising:

a) providing a computer-based system for analyzing nucleic acid sequence data, the system comprising a data storage medium having recorded thereon at least three independent nucleic acid sequences corresponding to at least portions of at least one gene, a set of instructions allowing analysis of the sequences to identify sequence differences between the at least three independent sequences and to distinguish true variances from sequence errors, and an output device;

b) analyzing at least three independent sequences; and c) outputting results of the analyzing to the output device, wherein the analysis step comprises comparing the at least three electronic nucleic acid sequences to identify sequence differences between the sequences;

identifying and discounting sequence differences in portions of the sequences wherein the number of sequence differences in an analysis window exceeds a predetermined limit;

identifying and discounting sequence differences that are part of consecutive mismatches;

assigning sequence differences a probability of representing a true variance based on sequence context; and utilizing the detection of particular sequence differences at the same sites in more than multiple sequences as an indication that each such sequence difference represents a true variance, wherein the result is a score derived from the probability that a detected sequence difference represents a true variance.

16. The method of claim 15, wherein said analysis comprises comparing said at least five electronic nucleic acid sequences to identify sequence differences between said sequences;

identifying and discounting sequence differences in portions of said sequences wherein the number of sequence differences in an analysis window exceeds a predetermined limit;

identifying and discounting sequence differences that are part of consecutive mismatches;

assigning sequence differences a probability of representing a true variance based on sequence context; and utilizing the detection of particular sequence differences at the same sites in more than multiple sequences as an indication that each such sequence difference represents a true variance, wherein the result is a score derived from the probability that a detected sequence difference represents a true variance.

17. A set of instructions on a computer-readable medium for computer-based identification of sequence variances in nucleotide sequences, wherein the set of instructions provides sequence comparisons of at least three independent sequences of at least portions of a selected gene; and a set of filters to distinguish true variances from sequence errors, the filters including a filter to identify and discount consecutive mismatches and at least one of:

a filter to identify low quality sequence regions;

a filter to identify adjacent base changes;

a filter to characterize the probability of sequence error or probability of true variance based on sequence context; and a filter utilizing the detection of particular sequence differences at the same sites in multiple sequences as an indication that each such sequence difference represents a true variance, whereby execution of the set of instructions on the at least three independent sequences provides a result indicative of the probability that a sequence difference detected between the sequences represents a true variance.

18. The method of claim 1, wherein said analyzing comprises:

identifying and discounting sequence differences in portions of said sequences wherein the number of sequence differences in an analysis window exceeds a predetermined limit;

identifying and discounting consecutive mismatches;

assigning sequence differences a probability of representing a true variance based on the identity of the adjacent upstream nucleotide or nucleotide sequence; and utilizing the detection of particular sequence differences at the same sites in multiple sequences as an indication that each such sequence difference represents a true variance, wherein the result is a score derived from the probability that a detected sequence difference represents a true variance.

19. The method of claim 1 wherein the analyzing utilizes a set of instructions performed on a computer-readable medium.

* * * * *

UNITED STATES PATENT AND TRADEMARK OFFICE
CERTIFICATE OF CORRECTION

PATENT NO. : 6,401,043 B1 Page 1 of 1
DATED : June 4, 2002
INVENTOR(S) : Vincent P. Stanton, Jr., R. Mark Adams, and David Steffan It is certified that error appears in the above-identified patent and that said Letters Patent is hereby corrected as shown below:

Column 11,
Line 29, remove "." above the "s" in "designated"
Line 40, change "altering" to -- filtering --

Column 13,
Line 13, change "fall" to -- full --

Column 14,
Lines 5 and 37, change "fall" to -- full --

Column 15,
Line 23, change "firer" to -- further --
Line 65, change "I" to -- 1 --

Column 19,
Line 21, change "legs" to -- less --

Column 23,
Line 67, change "UniGone" to -- UniGene --

Column 25,
Line 2, remove "," after "acid"

Signed and Sealed this

Fourteenth Day of January, 2003

JAMES E. ROGAN
*Director of the United States Patent and Trademark Office*